United States Patent [19]

Brenner

[11] 4,117,128
[45] Sep. 26, 1978

[54] SULFONYL BENZOFURANS AND BENZOTHIOPHENES HAVING CORONARY VASODILATOR ACTIVITY

[75] Inventor: L. Martin Brenner, Havertown, Pa.

[73] Assignee: SmithKline Corporation, Philadelphia, Pa.

[21] Appl. No.: 711,332

[22] Filed: Aug. 3, 1976

[51] Int. Cl.$^2$ .................. C07D 307/82; A61K 31/34; A61K 31/38
[52] U.S. Cl. ............................. 424/248.5; 424/250; 424/267; 424/274; 424/248.51; 424/275; 424/285; 260/293.57; 260/293.58; 260/326.5 SA; 260/326.5 SF; 260/330.5; 260/346.73; 544/146; 544/15 B; 544/376
[58] Field of Search .................... 260/346.2 R, 330.5, 260/326.5 SA, 326.5 SF, 293.57, 293.58, 268 BC, 247.1 P, 247.1 S; 424/248, 250, 267, 274, 275, 285, 248.5, 248.51

[56] References Cited

U.S. PATENT DOCUMENTS

| 3,248,401 | 4/1966 | Tondeur et al. | 260/346.2 R |
| 3,880,891 | 4/1975 | Hill et al. | 260/346.2 R |
| 3,947,470 | 3/1976 | Brenner et al. | 260/346.2 R |

FOREIGN PATENT DOCUMENTS

| 1,394,771 | 3/1965 | France. |
| 2,265,358 | 3/1975 | France. |

OTHER PUBLICATIONS

Burger, Medicinal Chem. 2nd. Ed., Interscience (1960) Chapter 8, pp. 72–88 (pp. 74 and 81 especially).

Primary Examiner—Henry R. Jiles
Assistant Examiner—Bernard Dentz
Attorney, Agent, or Firm—Janice E. Williams; William H. Edgerton; Alan D. Lourie

[57] ABSTRACT

The compounds are sulfonyl benzofurans and benzothiophenes having pharmacological activity, in particular, coronary vasodilator activity useful for the treatment of *angina pectoris*.

11 Claims, No Drawings

SULFONYL BENZOFURANS AND BENZOTHIOPHENES HAVING CORONARY VASODILATOR ACTIVITY

This invention relates to new sulfonyl benzofurans and benzothiophenes which have useful pharmacological activity. More specifically, these compounds have coronary vasodilator activity and are useful in the treatment of *angina pectoris*.

The sulfonyl benzofurans and benzothiophenes of this invention are represented by the following structural formula:

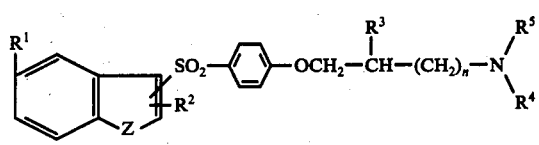

I or a pharmaceutically acceptable acid addition salt thereof, in which:

$R^1$ is hydrogen, halo or lower alkyl;

$R^2$ is lower alkyl, phenyl, benzyl, lower alkylphenyl, halophenyl, trifluoromethylphenyl, lower alkylbenzyl, halobenzyl or trifluoromethylbenzyl;

$R^3$ is hydrogen or hydroxy;

$R^4$ is hydrogen or lower alkyl and $R^5$ is lower alkyl or $R^4$ and $R^5$ together with the nitrogen atom to which they are attached form a pyrrolidine, piperidine, N-(lower alkyl)piperazine, morpholine or perhydroazepine ring;

n is 0 or 1 when $R^3$ is hydrogen and 1 when $R^3$ is hydroxy; and

Z is oxygen or sulfur.

As used herein, the term "lower alkyl" denotes groups having from one to four carbon atoms; "halo" refers to chloro, bromo and fluoro.

The compounds represented by formula I where Z is oxygen constitute one group of compounds of this invention; another such group is that where Z is sulfur.

Representative of the compounds of formula I are those where $R^1$ is hydrogen, $R^2$ is phenyl or n-butyl, $R^4$ is hydrogen or lower alkyl and $R^5$ is lower alkyl.

Examples of the compounds of this invention represented by formula I are 3-[4-(3-diethylaminopropoxy)phenylsulfonyl]-2-phenylbenzofuran, 2-n-butyl-3-[4-(2-diethylaminoethoxy)phenylsulfonyl]benzofuran, 2-n-butyl-3-[4-(2-hydroxy-3-isopropylaminopropoxy)phenylsulfonyl]benzofuran and 3-[4-(3-di-n-butylaminopropoxy)phenylsulfonyl]-2-phenylbenzofuran.

The compounds of formula I where $R^3$ is hydrogen are prepared as shown below where $R^1$, $R^2$, $R^4$, $R^5$ and Z are defined as above, p is 2 or 3 and X is halo, preferably chloro, or a leaving group such as tosyl or mesyl:

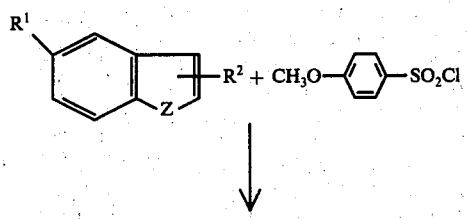

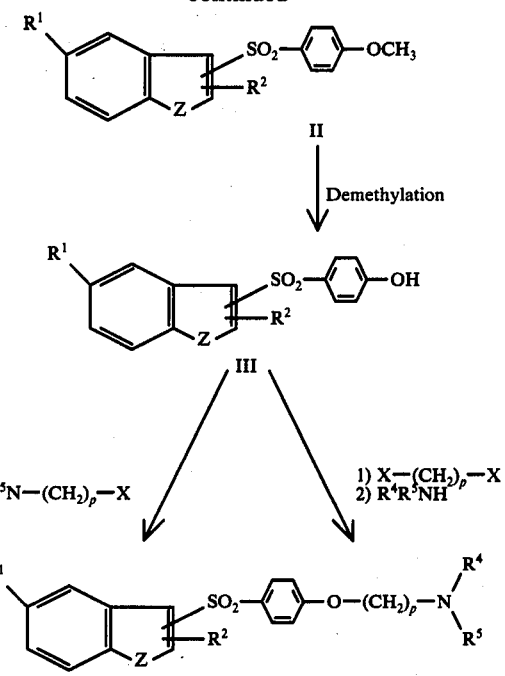

Thus, a benzofuran or benzothiophene nucleus is acylated with 4-methoxybenzenesulfonyl chloride by standard procedures, for example in the presence of stannic chloride in a solvent such as methylene chloride at a temperature of from about 0° C. to the reflux temperature of the solvent to give a methoxyphenylsulfonyl benzofuran or benzothiophene of formula II. Demethylation of II by known methods, for example by use of pyridine hydrochloride or boron tribromide, gives the corresponding hydroxyphenylsulfonyl benzofuran or benzothiophene of formula III.

Reaction of the sodium salt of III, prepared by treatment of III with sodium methoxide in methanol, with a substituted aminoalkyl halide, tosylate or other equivalent compound of the formula $R^4R^5N—(CH_2)_p—X$, where $R^4$, $R^5$, p and X are defined as above, in the presence of a base such as potassium carbonate in a solvent such as toluene or acetone at a temperature of about 25° C. to the reflux temperature of the solvent for about 1 to about 24 hours gives the corresponding compounds of formula I where $R^3$ is hydrogen and n is 0 or 1. These compounds are also prepared by reaction of III with a dihaloalkane of the formula $X—(CH_2)_p—X$ where X is defined as above in the presence of a base such as potassium carbonate in a solvent such as acetone, preferably at the reflux temperature of the solvent, followed by reaction of the product thus formed with an amine of the formula $R^4R^5NH$, where $R^4$ and $R^5$ are defined as above in a solvent such as ethanol at a temperature at or above the reflux temperature of the solvent.

When $R^3$ is hydroxy and n is 1, the compounds of formula I are prepared from the corresponding compounds of formula III as follows where $R^1$, $R^2$, $R^4$ and $R^5$ are defined as above:

III 

-continued

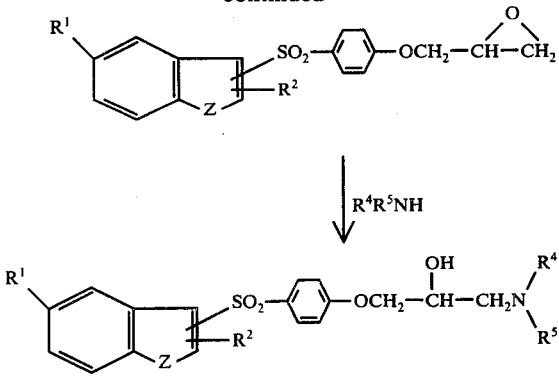

As outlined above, reaction of III with an epihalohydrin such as epichlorohydrin or epibromohydrin in the presence of a base such as potassium carbonate or sodium hydroxide in a solvent such as ethanol or acetone followed by ring opening of the epoxy intermediate thus formed with an excess amount of an amine of the formula $R^4R^5NH$ in a minimum amount of a solvent such as ethanol or with excess amine as solvent at a temperature of from about 25° to about 125° for about 30 minutes to about 12 hours gives the corresponding compounds of formula I where $R^3$ is hydroxy and $n$ is 1.

The products of formula I are isolated and purified as such by standard techniques including solvent extraction, crystallization and chromatographic methods or as the corresponding acid addition salts which are also objects of this invention. The salts are formed with organic and inorganic acids according to methods known to the art. Thus, a solution of the amine in ether, chloroform or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether, with the desired salt separating directly. Exemplary of such organic salts are those with maleic, fumaric, benzoic, ascorbic, pamoic, succinic, hexamic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

The benzofuran and benzothiophene starting materials are known to the art.

Some of the compounds of this invention may exist as optical isomers due to an asymmetric carbon atom in the aminoalkoxy side chain. All of the isomers, including separated isomers and mixtures thereof, are included within the scope of this invention.

The coronary vasodilator activity and hypotensive effects of the compounds of this invention are demonstrated in dogs by an increase in coronary blood flow with concomitant decrease of mean arterial blood pressure upon intravenous administration of doses of from about 0.63 to about 10.0 mg./kg. These parameters are measured as follows:

Adult mongrel dogs (13–16 kg.) are pretreated with 2 mg./kg. s.c. of morphine sulfate followed in one hour by intravenous administration of 1–1.5 ml./kg. of an aqueous solution containing 1.5% chloralose and 20% urethane. Supplemental doses of morphine and chloraloseurethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic flowmeter and Flo-Probe (MDS).

Pharmaceutical compositions having coronary vasodilator activity comprising a pharmaceutical carrier and a compound of formula I and methods of producing coronary vasodilation by administering these compounds are also objects of this invention.

The pharmacologically active compounds of this invention may be administered orally or parenterally in an amount to produce the desired activity.

Preferably the compounds are administered in conventional dosage unit forms prepared by combining an appropriate dose of the compound with standard pharmaceutical carriers. The dosage units will contain the active ingredient in an amount of from about 100 mg. to about 600 mg., preferably 150 mg. to 300 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of producing coronary vasodilator activity in accordance with this invention comprises administering internally to an animal an effective amount of a compound of formula I. The compound will preferably be administered in a dosage unit form as described above orally or parenterally, the oral route being preferred. Advantageously equal doses will be administered one to two times daily with the daily dosage regimen being from about 200 mg. to about 1200 mg., preferably from about 300 mg. to about 600 mg. When the method described above is carried out, coronary vasodilator activity is produced.

One skilled in the art will recognize that in determining the amounts of the compound needed to produce the desired pharmacological effect without toxic side effects, the activity of the compound as well as the size of the host animal must be considered.

The following examples illustrate the invention but are not to be construed as limiting the scope thereof. Temperatures are in degrees Centigrade unless otherwise stated.

When formed, acid addition salts may be converted to the corresponding free amines by treating a solution of the salt in a solvent such as water, a chloroform-water or a benzene-water mixture with a base such as 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through a chloride ion exchange column.

EXAMPLE 1

3-[4-(3-Diethylaminopropoxy)phenylsulfonyl]-2-phenylbenzofuran

To a solution of 3.9 g.(0.02 mol.) of 2-phenylbenzofuran and 6.2 g. (0.03 mol.) of 4-methoxybenzenesulfonyl chloride in 50 ml. of methylene chloride was added 3.5 ml. (7.83 g., 0.03 mol.) of stannic chloride. The reaction mixture was stirred at ambient temperature for about 12 hours then poured into 150. ml. of water. The layers were separated and the organic phase was extracted once with 10% aqueous sodium bicarbonate solution, three times with water and once with a saturated sodium chloride solution, dried (MgSO$_4$) and evaporated to dryness to give a residue. Ether (ca. 35 ml.) was added to the residue and it was refluxed for 1 hour then filtered. The solid collected was recrystallized from benzene-hexane then chromatographed on a silica gel "dry column" with methylene chloride as eluant to give 3-(4-methoxyphenylsulfonyl)-2-phenylbenzofuran, m.p. 146°–148°.

3-(4-Methoxyphenylsulfonyl)-2-phenylbenzofuran (1.9 g.) was combined with 12 g. of freshly distilled pyridine hydrochloride and heated at 210° for 3.5 hours. The hot mixture was poured onto an ice-dilute hydrochloric acid mixture and the precipitate formed was collected by filtration and dissolved in chloroform. The chloroform solution was extracted three times with water and then with a saturated sodium chloride solution, refluxed with decolorizing charcoal, filtered and dried (MgSO$_4$). Evaporation of the solvent gave 3-(4-hydroxyphenylsulfonyl)-2-phenylbenzofuran, m.p. 166°–168°.

A solution of 0.14 g. (0.006 g.-atom) of sodium in 20 ml. of methanol was added to a solution of 1.1 g. (0.003 mol.) of 3-(4-hydroxyphenylsulfonyl)-2-phenylbenzofuran in 25 ml. of dry methanol and the mixture was refluxed for 0.5 hour. The solvent was evaporated and 25 ml. of toluene and 3 ml. of dimethylformamide were added to the residue. A solution of 0.86 g. (0.006 mol.) of 3-diethylaminopropyl chloride in 10 ml. of toluene was added dropwise and the mixture was refluxed for 2.5 hours. An additional 0.162 g. (0.003 mol.) of sodium methoxide and 0.43 g. (0.003 mol.) of 3-diethylaminopropyl chloride were added and the mixture was refluxed for ca. 16 hours. The mixture was filtered, water and methylene chloride were added and the layers were separated. The aqueous phase was extracted with methylene chloride and the organic phase was extracted with water and saturated sodium chloride solution. The organic layers were combined, dried (MgSO$_4$) and evaporated to dryness to give the title compound.

3-[4-(3-Diethylaminopropoxy)phenylsulfonyl]-2-phenylbenzofuran was dissolved in ether and an ethereal solution of hydrochloric acid was added. The mixture was stirred for ca. 16 hours then chromatographed on silica gel with 9:1 chloroform-methanol as eluant to give the title compound as the hydrochloride salt, m.p. 120°–125°.

EXAMPLE 2

2-n-Butyl-3-[4-(2-diethylaminoethoxy)phenylsulfonyl]benzofuran

To a solution of 4.35 g. (0.025 mol.) of 2-n-butylbenzofuran in 25 ml. of methylene chloride was added a solution of 5.16 g. (0.025 mol.) of 4-methoxybenzenesulfonyl chloride in 50 ml. of methylene chloride. The resulting solution was cooled to 0° and 6.9 g. (0.026 mol.) of stannic chloride was added dropwise. The reaction mixture was stirred for 30 minutes in the cold, for 1.5 hours at ambient temperature, then refluxed for ca. 60 hours. The mixture was poured into 200 ml. of water and stirred for 5 minutes. The layers were separated and the organic phase was extracted three times with water. Sodium hydroxide solution (ca. 1%) was added to the organic layer and it was stirred at ambient temperature for 1 hour. The layers were separated and the organic phase was washed three times with water and once with a saturated sodium chloride solution, dried (MgSO$_4$) and evaporated to dryness to give a residue which was chromatographed on a silica gel "dry column" with 9:1 methylene chloride-ether as eluant to give 2-n-butyl-3-(4-methoxyphenylsulfonyl)benzofuran.

2-n-Butyl-3-(4-methoxyphenylsulfonyl)benzofuran was demethylated with pyridine hydrochloride at 185° according to the procedure described in Example 1 to give 2-n-butyl-3-(4-hydroxyphenylsulfonyl)benzofuran, m.p. 163°–165°.

To a solution of 1.4 g. (0.0042 mol.) of 2-n-butyl-3-(4-hydroxyphenylsulfonyl)benzofuran in 20 ml. of methanol was added 25 ml. of methanol containing 110 mg. (0.0048 g.-atom) of sodium. The reaction mixture was heated on a steam bath for 30 minutes then evaporated to dryness. The residue was dissolved in 25 ml. of toluene and ca. 1 ml. of methanol, a suspension of 0.615 g. (0.0048 mol.) of distilled 2-diethylaminoethyl chloride in 15 ml. of toluene was added and the resulting mixture was heated on a steam bath for 3 hours. The solution was filtered through MgSO$_4$ and chromatographed on silica gel with 50:50 ether-acetone to give the title compound.

The title compound was converted to the corresponding hydrochloride salt as described in the procedure of Example 1.

EXAMPLE 3

2-n-Butyl-3-[4-(2-hydroxy-3-isopropylaminopropoxy)-phenylsulfonyl]benzofuran 2-n-Butyl-3-(4-hydroxyphenylsulfonyl)benzofuran (1.5 g., 0.0045 mol.) was dissolved in 40 ml. of dry acetone containing 2.5 g. (0.018 mol.) of potassium carbonate and 2.46 g. (0.018 mol.) of epibromohydrin. The mixture was refluxed for ca. 16 hours then filtered. The solvent and excess epibromohydrin were removed in vacuo to give 2-n-butyl-3-[4-(2,3-epoxypropoxy)-phenylsulfonyl]benzofuran.

2-n-Butyl-3-[4-(2,3-epoxypropoxy)phenylsulfonyl]benzofuran (1.9 g.) was dissolved in 30 ml. of freshly distilled isopropylamine and the solution was heated at 100° for 2 hours. After cooling, the solvent was evaporated to give a residue which was dissolved in chloroform. Evaporation of the solvent gave the title compound.

The title compound was converted to the corresponding hydrochloride salt by dissolving the free amine in methylene chloride and acidifying with an ethereal solution of hydrochloric acid. Evaporation of the solvent gave a residue which was recrystallized from ethyl acetate to give 2-n-butyl-3-[4-(2-hydroxy-3-isopropylaminopropoxy)phenylsulfonyl]benzofuran hydrochloride, m.p. 120°–125°.

EXAMPLE 4

3-[4-(3-Di-n-butylaminopropoxy)phenylsulfonyl]-2-phenylbenzofuran

To a solution of 0.85 g. (0.0024 mol.) of 3-(4-hydroxyphenylsulfonyl)-2-phenylbenzofuran in 25 ml. of dry acetone was added 0.96 g. (0.0048 mol.) of 1,3-dibromopropane and 0.66 g. (0.0048 mol.) of potassium carbonate. The mixture was refluxed for ca. 12 hours, then an additional 0.4 g. of 1,3-dibromopropane, 0.3 g. of potassium carbonate and 25 ml. of dry acetone were added and the mixture was refluxed for 5 hours. The reaction mixture was filtered and the solvent was removed in vacuo to give a residue which was dissolved in 2–4 ml. of ethanol to which 22–24 ml. of freshly distilled di-n-butylamine was added. The mixture was heated at 130° for 4 hours, then cooled and diluted with ethanol. The solvent and excess amine were removed by evaporation to give 0.23 g. of the title compound.

3-[4-(3-Di-n-butylaminopropoxy)phenylsulfonyl]-2-phenylbenzofuran was dissolved in ether and an ethereal solution of hydrochloric acid was added. The ether was decanted and the oily material was washed with ether and dissolved in chloroform. The chloroform solution was extracted four times with water and once with a saturated sodium chloride solution, dried (MgSO$_4$) and evaporated to dryness to give a residue which was chromatographed on silica gel with chloroform-methanol as eluant to give the title compound as the corresponding hydrochloride salt.

EXAMPLE 5

When 3-(4-hydroxyphenylsulfonyl)-2-phenylbenzofuran is reacted with 3-dimethylaminopropyl chloride by the procedure described in Example 1, 3-[4-(3-dimethylaminopropoxy)phenylsulfonyl]-2-phenylbenzofuran is obtained.

3-[4-(3-Dimethylaminopropoxy)phenylsulfonyl]-2-phenylbenzofuran is converted to the corresponding hydrochloride salt as described above.

Similarly, 3-[4-(3-di-n-propylaminopropoxy)phenylsulfonyl]-2-phenylbenzofuran is prepared by substitution of 3-di-n-propylaminopropyl chloride in the procedure of Example 1 in place of 3-diethylaminopropyl chloride.

Treatment of 3-[4-(3-di-n-propylaminopropoxy)-phenylsulfonyl]-2-phenylbenzofuran with ethereal hydrochloric acid as previously described gives the corresponding hydrochloric acid salt.

EXAMPLE 6

5-Chloro-3-[4-(3-diethylaminopropoxy)phenylsulfonyl]-2-phenylbenzofuran

Acylation of 5-chloro-2-phenylbenzofuran with 4-methoxybenzenesulfonyl chloride as described in Example 1 followed by demethylation of the 5-chloro-3-(4-methoxyphenylsulfonyl)-2-phenylbenzofuran thus formed also as described therein, gives 5-chloro-3-(4-hydroxyphenylsulfonyl)-2-phenylbenzofuran.

Reaction of 5-chloro-3-(4-hydroxyphenylsulfonyl)-2-phenylbenzofuran with 3-diethylaminopropyl chloride according to the procedure of Example 1 gives the title compound.

The title compound is converted to the corresponding hydrochloride salt by reaction with an ethereal solution of hydrochloric acid as described above.

EXAMPLE 7

2-(4-Chlorophenyl)-3-[4-(3-diethylaminopropoxy)-phenylsulfonyl]benzofuran

Acylation of 2-(p-chlorophenyl)benzofuran with 4-methoxybenzenesulfonyl chloride as described in Example 1 followed by demethylation of the 2-(4-chlorophenyl)-3-(4-methoxyphenylsulfonyl)benzofuran thus formed also as described therein, gives 2-(4-chlorophenyl)-3-(4-hydroxyphenylsulfonyl)benzofuran.

Reaction of 2-(4-chlorophenyl)-3-(4-hydroxyphenylsulfonyl)benzofuran with 3-diethylaminopropyl chloride according to the procedure of Example 1 gives the title compound.

EXAMPLE 8

3-[4-(3-Diethylaminopropoxy)phenylsulfonyl]-2-(4-tolyl)benzofuran 3-(4-Hydroxyphenylsulfonyl)-2-(4-tolyl)benzofuran is prepared by acylation of 2-(4-tolyl)benzofuran with 4-methoxybenzenesulfonyl chloride followed by demethylation of the 3-(4-methoxyphenylsulfonyl)-2-(4-tolyl)benzofuran thus formed as described hereinabove.

Reaction of 3-(4-hydroxyphenylsulfonyl)-2-(4-tolyl)benzofuran with 3-diethylaminopropyl chloride according to the procedure described in Example 1 gives the title compound.

EXAMPLE 9

3-[4-(2-Diethylaminoethoxy)phenylsulfonyl]-2-(4-tolyl)benzofuran

Reaction of 3-(4-hydroxyphenylsulfonyl)-2-(4-tolyl)benzofuran with 2-diethylaminoethyl chloride according to the procedure of Example 1 gives the title compound.

EXAMPLE 10

2-Ethyl-3-[4-(2-diethylaminoethoxy)phenylsulfonyl]benzofuran

2-Ethyl-3-(4-hydroxyphenylsulfonyl)benzofuran is prepared by acylation of 2-ethylbenzofuran with 4-methoxybenzenesulfonyl chloride followed by demethylation of the 2-ethyl-3-(4-methoxyphenylsulfonyl)benzofuran thus formed as described hereinabove.

Reaction of 2-ethyl-3-(4-hydroxyphenylsulfonyl)benzofuran with 2-diethylaminoethyl chloride by the procedure described in Example 1 gives the title compound.

EXAMPLE 11

2-[4-(3-Diethylaminopropoxy)phenylsulfonyl]-3-phenylbenzofuran

Acylation of 3-phenylbenzofuran with 4-methoxybenzenesulfonyl chloride as described hereinabove followed by demethylation of the 2-(4-methoxyphenylsulfonyl)-3-phenylbenzofuran thus formed as previously described gives 2-(4-hydroxyphenylsulfonyl)-3-phenylbenzofuran.

Reaction of 2-(4-hydroxyphenylsulfonyl)-3-phenylbenzofuran with 3-diethylaminopropyl chloride according to the procedure of Example 1 gives the title compound.

EXAMPLE 12

2-[4-(2-hydroxy-3-isopropylaminopropoxy)phenylsulfonyl]-3-phenylbenzofuran

Reaction of 2-(4-hydroxyphenylsulfonyl)-3-phenylbenzofuran with epibromohydrin according to the procedure of Example 3 gives 2-[4-(2,3-epoxypropoxy)phenylsulfonyl]-3-phenylbenzofuran.

Treatment of 2-[(4-(2,3-epoxypropoxy)phenylsulfonyl]-3-phenylbenzofuran with isopropylamine as described in Example 3 gives the title compound.

EXAMPLE 13

3-(4-Chlorophenyl)-2-[4-(3-diethylaminopropoxy)phenylsulfonyl]benzofuran

Acylation of 3-(3-chlorophenyl)benzofuran with 4-methoxybenzenesulfonyl chloride as described hereinabove followed by demethylation of the product formed also as described above gives 3-(4-chlorophenyl)-2-(4-hydroxyphenylsulfonyl)benzofuran.

Reaction of 3-(4-chlorophenyl)-2-(4-hydroxyphenylsulfonyl)benzofuran with 3-diethylaminopropyl chloride by the method described in Example 1 gives the title compound.

EXAMPLE 14

2-(4-Chlorobenzyl)-3-[4-(3-diethylaminopropoxy)phenylsulfonyl]benzofuran 2-(4-Chlorobenzyl)-3-(4-hydroxyphenylsulfonyl)benzofuran is prepared by acylation of 2-(4-chlorobenzyl)benzofuran with 4-methoxybenzenesulfonyl chloride with subsequent demethylation of the product thus formed with pyridine hydrochloride, all as described in Example 1.

Reaction of 2-(4-chlorobenzyl)-3-(4-hydroxyphenylsulfonyl)benzofuran with 3-diethylaminopropyl chloride by procedures described hereinabove gives the title compound.

EXAMPLE 15

3-[4-(3-Diethylaminopropoxy)phenylsulfonyl]-2-(3-trifluoromethylbenzyl)benzofuran Acylation of 2-(3-trifluoromethylbenzyl)benzofuran with 4-methoxybenzenesulfonyl chloride as described in the procedure described above followed by demethylation of the 3-(4-methoxyphenylsulfonyl)-2-(3-trifluoromethylbenzyl)benzofuran thus formed also as described above gives 3-(4-hydroxyphenylsulfonyl)-2-(3-trifluoromethylbenzyl)benzofuran.

Reaction of 3-(4-hydroxyphenylsulfonyl)-2-(3-trifluoromethylbenzyl)benzofuran with 3-diethylaminopropyl chloride as described above gives the title compound.

EXAMPLE 16

2-Benzyl-3-[4-(3-diethylaminopropoxy)phenylsulfonyl]benzofuran

When 2-benzylbenzofuran is used as a starting material in the procedure of Example 1 in place of 2-phenylbenzofuran and the resulting product is demethylated then reacted with 3-diethylaminopropyl chloride, the title compound is ultimately prepared.

EXAMPLE 17

3-[4-(3-Diethylaminopropoxy)phenylsulfonyl]-2-(2-fluorophenyl)benzofuran

Substitution of 2-(2-fluorophenyl)benzofuran in the procedure of Example 1 for 2-phenylbenzofuran followed by demethylation of the 2-(2-fluorophenyl)-3-(4-methoxyphenylsulfonyl)benzofuran thus formed and reaction of the resulting product with 3-diethylaminopropyl chloride as described therein gives the title compound.

EXAMPLE 18

Acylation of a benzylbenzofuran listed below:

2-(4-methylbenzyl)benzofuran
2-(4-ethylbenzyl)benzofuran
2-(4-fluorobenzyl)benzofuran with 4-methoxybenzenesulfonyl chloride followed by demethylation of the product thus formed and reaction of the resulting 2-(substituted benzyl)-3-(4-hydroxyphenylsulfonyl)benzofuran with 3-diethylaminopropyl chloride according to procedures described hereinabove gives the following compounds of this invention:

3-[4-(3-diethylaminopropoxy)phenylsulfonyl]-2-(4-methylbenzyl)benzofuran
3-[4-(3-diethylaminopropoxy)phenylsulfonyl]-2-(4-ethylbenzyl)benzofuran
3-[4-(3-diethylaminopropoxy)phenylsulfonyl]-2-(4-fluorobenzyl)benzofuran

EXAMPLE 19

2-Benzyl-5-bromo-3-[4-(3-diethylaminopropoxy)phenylsulfonyl]benzofuran

2-Benzyl-5-bromobenzofuran is acylated with 4-methoxyenzenesulfonyl chloride as described above and the resulting 2-benzyl-5-bromo-3-(4-methoxyphenylsulfonyl)benzofuran is demethylated to give 2-benzyl-5-bromo-3-(4-hydroxyphenylsulfonyl)benzofuran.

Reaction of 2-benzyl-5-bromo-3-(4-hydroxyphenylsulfonyl)benzofuran with 3-diethylaminopropyl chloride as previously described gives the title compound.

EXAMPLE 20

2-Benzyl-3-[4-(3-diethylaminopropoxy)phenylsulfonyl]-5-ethylbenzofuran

Acylation of 2-benzyl-5-ethylbenzofuran with 4-methoxybenzenesulfonyl chloride followed by demethylation of the product thus formed as previously described gives 2-benzyl-5-ethyl-3-(4-hydroxyphenylsulfonyl)benzofuran.

Reaction of 2-benzyl-5-ethyl-3-(4-hydroxyphenylsulfonyl)benzofuran with 3-diethylaminopropyl chloride as described above gives the title compound.

EXAMPLE 21

When a substituted benzofuran listed below:

5-fluoro-3-phenylbenzofuran
2-(4-ethylphenyl)benzofuran
2-(3-t-butylphenyl)benzofuran
2-(4-fluorophenyl)benzofuran
2-(4-trifluoromethylphenyl)benzofuran is acylated with 4-methoxybenzenesulfonyl chloride and the product thus formed is demethylated as previously described hereinabove, the following compounds are obtained:

5-fluoro-2-(4-hydroxyphenylsulfonyl)-3-phenylbenzofuran
2-(4-ethylphenyl)-3-(4-hydroxyphenylsulfonyl)benzofuran
2-(3-t-butylphenyl)-3-(4-hydroxyphenylsulfonyl)benzofuran
2-(4-fluorophenyl)-3-(4-hydroxyphenylsulfonyl)benzofuran
3-(4-hydroxyphenylsulfonyl)-2-(4-trifluoromethylphenyl)benzofuran.

Reaction of a hydroxyphenylsulfonylbenzofuran listed above with 3-diethylaminopropyl chloride according to procedures described hereinabove gives the following compounds of this invention:

3-[4-(3-diethylaminopropoxy)phenylsulfonyl]-5-fluoro-3-phenylbenzofuran
3-[4-(3-diethylaminopropoxy)phenylsulfonyl]-2-(4-ethylphenyl)benzofuran
2-(3-t-butylphenyl)-3-[4-(3-diethylaminopropoxy)phenylsulfonyl]benzofuran
3-[4-(3-diethylaminopropoxy)phenylsulfonyl]-2-(4-fluorophenyl)benzofuran
3-[4-(3-diethylaminopropoxy)phenylsulfonyl]-2-(4-trifluoromethylphenyl)benzofuran.

EXAMPLE 22

Treatment of 3-(4-hydroxyphenylsulfonyl)-2-phenylbenzofuran with a chloroalkylamine listed below:

N-(3-chloropropyl)piperidine
N-(2-chloroethyl)pyrrolidine
N-(2-chloroethyl)morpholine according to procedures described hereinabove gives the following compounds of this invention:

2-phenyl-3-[4-(3-N-piperidinopropoxy)phenylsulfonyl]benzofuran
2-phenyl-3-[4-(2-N-pyrrolidinoethoxy)phenylsulfonyl]benzofuran
3-[4-(2-N-morpholinoethoxy)phenylsulfonyl]-2-phenylbenzofuran.

EXAMPLE 23

Reaction of 2-n-butyl-3-[4-(2,3-epoxypropoxy)phenylsulfonyl]benzofuran with an amine listed below:

methylamine
ethylamine
butylamine
dimethylamine
diethylamine
dipropylamine according to the procedure described in Example 3 gives the following compounds of this invention:

2-n-butyl-3-[4-(2-hydroxy-3-methylaminopropoxy)phenylsulfonyl]benzofuran
2-n-butyl-3-[4-(2-hydroxy-3-ethylaminopropoxy)phenylsulfonyl]benzofuran
2-n-butyl-3-[4-(2-hydroxy-3-butylaminopropoxy)phenylsulfonyl]benzofuran
2-n-butyl-3-[4-(2-hydroxy-3-dimethylaminopropoxy)phenylsulfonyl]benzofuran
2-n-butyl-3-[4-(2-hydroxy-3-diethylaminopropoxy)phenylsulfonyl]benzofuran
2-n-butyl-3-[4-(2-hydroxy-3-dipropylaminopropoxy)phenylsulfonyl]benzofuran.

EXAMPLE 24

Reaction of 2-[4-(2,3-epoxypropoxy)phenylsulfonyl]-3-phenylbenzofuran with an amine listed below:

piperidine
pyrrolidine
morpholine
N-methylpiperazine
perhydroazepine as described in the procedure of Example 3 gives the following compounds of this invention:

2-[4-(2-hydroxy-3-N-piperidinopropoxy)phenylsulfonyl]-3-phenylbenzofuran
2-[4-(2-hydroxy-3-N-pyrrolidinopropoxy)phenylsulfonyl]-3-phenylbenzofuran
2-[4-(2-hydroxy-3-N-morpholinopropoxy)phenylsulfonyl]-3-phenylbenzofuran
2-[4-(2-hydroxy-3-N-methylpiperazinopropoxy)phenylsulfonyl]-3-phenylbenzofuran
2-[4-(2-hydroxy-3-N-perhydroazepinopropoxy)phenylsulfonyl]-3-phenylbenzofuran.

EXAMPLE 25

3-[4-(3-Diethylaminopropoxy)phenylsulfonyl]-2-phenylbenzothiophene

Acylation of 2-phenylbenzothiophene with 4-methoxybenzenesulfonyl chloride as described above gives 3-(4-methoxyphenylsulfonyl)-2-phenylbenzothiophene.

3-(4-Methoxyphenylsulfonyl)-2-phenylbenzothiophene is demethylated with pyridine hydrochloride as described above and the resulting product is reacted with 3-diethylaminopropyl chloride, also as described above, to give the title compound.

EXAMPLE 26

When an equivalent amount of a benzothiophene listed below:

3-phenylbenzothiophene
2-benzylbenzothiophene
5-chloro-3-phenylbenzothiophene is used as a starting material in the procedure of Example 25 in place of 2-phenylbenzothiophene, the following compounds of this invention are obtained as final products:

2-[4-(3-diethylaminopropoxy)phenylsulfonyl]-3-phenyl-benzothiophene
2-benzyl-3-[4-(3-diethylaminopropoxy)phenylsulfonyl]-benzothiophene
5-chloro-2-[4-(3-diethylaminopropoxy)phenylsulfonyl]-3-phenylbenzothiophene.

EXAMPLE 27

Addition of an ethereal solution of oxalic acid to a solution of 3-[4-(3-diethylaminopropoxy)phenylsulfonyl]-2-phenylbenzofuran in ether gives the oxalate salt.

The corresponding hydrochloride salt may be prepared from the oxalate salt by passage of a solution of 3-[4-(3-diethylaminopropoxy)phenylsulfonyl]-2-phenylbenzofuran oxalate in ethanol through an Amberlite IRA-401 chloride ion exchange column.

In a similar manner, other acid addition salts may be prepared.

EXAMPLE 28

| Ingredients | Amounts |
| --- | --- |
| 3-[4-(3-Diethylaminopropoxy)phenyl-sulfonyl]-2-phenylbenzofuran | 100 mg. |
| Calcium sulfate dihydrate | 150 mg. |
| Sucrose | 25 mg. |
| Starch | 15 mg. |
| Talc | 5 mg. |
| Stearic acid | 3 mg. |

The sucrose, calcium sulfate dihydrate and 3-[4-(3-diethylaminopropoxy)phenylsulfonyl]-2-phenylbenzofuran are thoroughly mixed and granulated with 10% gelatin solution. The wet granules are screened, dried and then mixed with the starch, talc and stearic acid, screened and compressed into a tablet.

EXAMPLE 29

| Ingredients | Amounts |
| --- | --- |
| 3-[4-(3-Diethylaminopropoxy)phenyl-sulfonyl]-2-phenylbenzofuran | 150 mg. |
| Magnesium stearate | 5 mg. |
| Lactose | 100 mg. |

The ingredients are mixed and filled into a hard gelatin capsule.

Similarly, other substituted benzofurans disclosed herein may be formulated into tablets and capsules by the procedures of Examples 28 and 29.

The compositions prepared as in Examples 28 and 29 are administered orally to a subject in need of coronary vasodilator activity within the dose ranges given hereabove.

What is claimed is:

1. A compound of the formula:

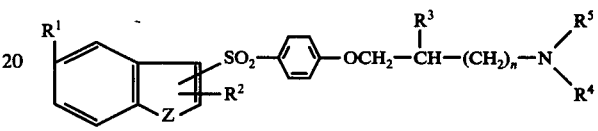

or a pharmaceutically acceptable acid addition salt thereof, in which:

$R^1$ is hydrogen, halo or lower alkyl;
$R^2$ is lower alkyl, phenyl, benzyl, lower alkylphenyl, halophenyl, trifluoromethylphenyl, lower alkylbenzyl, halobenzyl or trifluoromethylbenzyl;
$R^3$ is hydrogen or hydroxy;
$R^4$ is hydrogen or lower alkyl and $R^5$ is lower alkyl or $R^4$ and $R^5$ together with the nitrogen atom to which they are attached form a pyrrolidine, piperidine, N-(lower alkyl)piperazine, morpholine or perhydroazepine ring;
$n$ is 0 or 1 when $R^3$ is hydrogen and 1 when $R^3$ is hydroxy; and
Z is oxygen or sulfur.

2. A compound according to claim 1 in which Z is oxygen.

3. A compound according to claim 1 in which Z is sulfur.

4. A compound according to claim 2 in which $R^4$ is hydrogen or lower alkyl and $R^5$ is lower alkyl.

5. A compound according to claim 4 in which $R^2$ is phenyl or n-butyl.

6. A compound according to claim 5, said compound being 3-[4-(3-diethylaminopropoxy)phenylsulfonyl]-2-phenylbenzofuran.

7. A compound according to claim 5, said compound being 2-n-butyl-3-[4-(2-diethylaminoethoxy)phenylsulfonyl]benzofuran.

8. A compound according to claim 5, said compond being 2-n-butyl-3-[4-(2-hydroxy-3-isopropylaminopropoxy)phenylsulfonyl]benzofuran.

9. A compound according to claim 5, said compound being 3-[4-(3-di-n-butylaminopropoxy)phenylsulfonyl]-2-phenylbenzofuran.

10. A pharmaceutical composition having coronary vasodilator activity comprising a pharmaceutical carrier and a compound of claim 1 in an amount sufficient to produce said activity.

11. A method of producing coronary vasodilation comprising administering to an animal a compound of claim 1 in an amount sufficient to produce said activity.

* * * * *